(12) United States Patent
Rietzel et al.

(10) Patent No.: US 7,545,911 B2
(45) Date of Patent: Jun. 9, 2009

(54) IMAGING DEVICE AND THERAPY FACILITY HAVING SUCH A DEVICE

(75) Inventors: Eike Rietzel, Darmstadt (DE); Andres Sommer, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 47 days.

(21) Appl. No.: 11/593,930

(22) Filed: Nov. 7, 2006

(65) Prior Publication Data
US 2007/0135703 A1 Jun. 14, 2007

(30) Foreign Application Priority Data
Nov. 9, 2005 (DE) .................. 10 2005 053 488

(51) Int. Cl.
*A61N 5/10* (2006.01)
(52) U.S. Cl. .......................................... 378/65; 378/205
(58) Field of Classification Search ............... 378/4–20, 378/64–65, 207, 205
See application file for complete search history.

(56) References Cited

U.S. PATENT DOCUMENTS

| 5,638,419 A | 6/1997 | Ingwersen |
| 5,983,424 A | 11/1999 | Naslund |
| 6,366,796 B1 * | 4/2002 | Yanof et al. ................. 600/407 |
| 6,502,261 B1 | 1/2003 | Harwood |
| 2005/0070792 A1 * | 3/2005 | Mizukoshi et al. .......... 600/427 |
| 2005/0281374 A1 * | 12/2005 | Cheng et al. .................. 378/68 |
| 2007/0025524 A1 * | 2/2007 | Yue ............................. 378/205 |
| 2007/0064870 A1 * | 3/2007 | Herrmann et al. ............. 378/65 |
| 2007/0071168 A1 * | 3/2007 | Allison et al. ................. 378/65 |

FOREIGN PATENT DOCUMENTS

| DE | 195 05 276 A1 | 8/1996 |
| DE | 697 06 807 T2 | 4/2002 |

OTHER PUBLICATIONS

German Office Action for DE 10 2005 053 488.0-35 dated Aug. 22, 2006 and English translation.

* cited by examiner

*Primary Examiner*—Hoon Song
(74) *Attorney, Agent, or Firm*—Brinks, Hofer, Gilson & Lione

(57) ABSTRACT

An imaging device and therapy facility are provided. An imaging device includes a table that supports a patient. An image-making unit is operative to create digital picture data of a body region of the patient. The image-making unit is operative to three-dimensionally scale the coordinates of the picture data recorded with respect to a space coordinate system that is stationary with the table, with respect to a table coordinate system that is stationary with a patient support of the table, or with respect to both the space coordinate system and the table coordinate system.

20 Claims, 1 Drawing Sheet

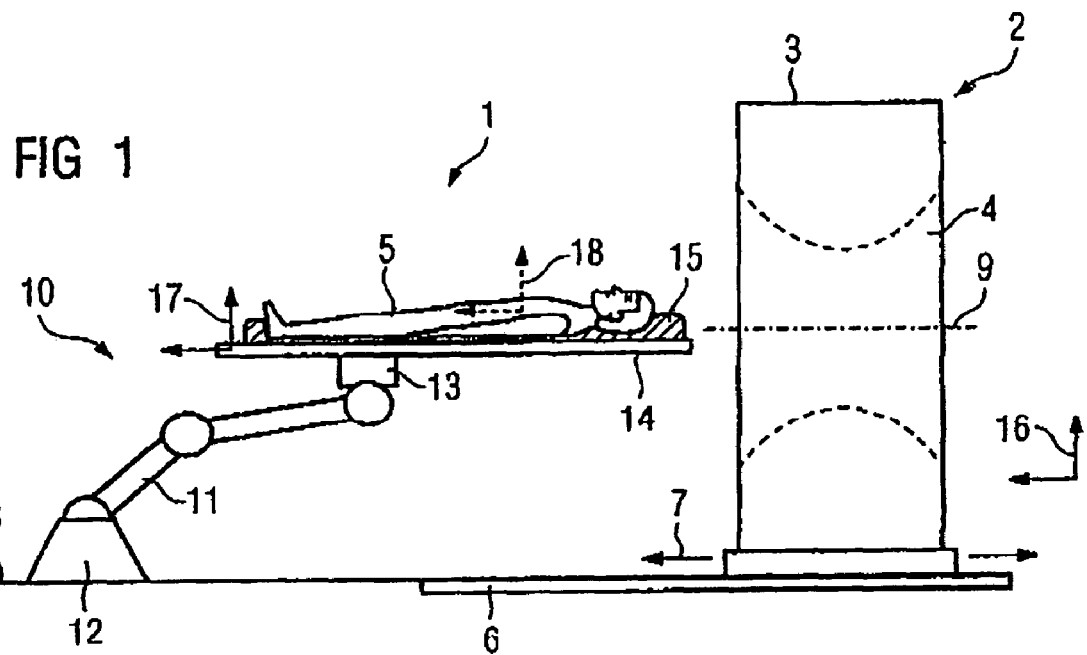
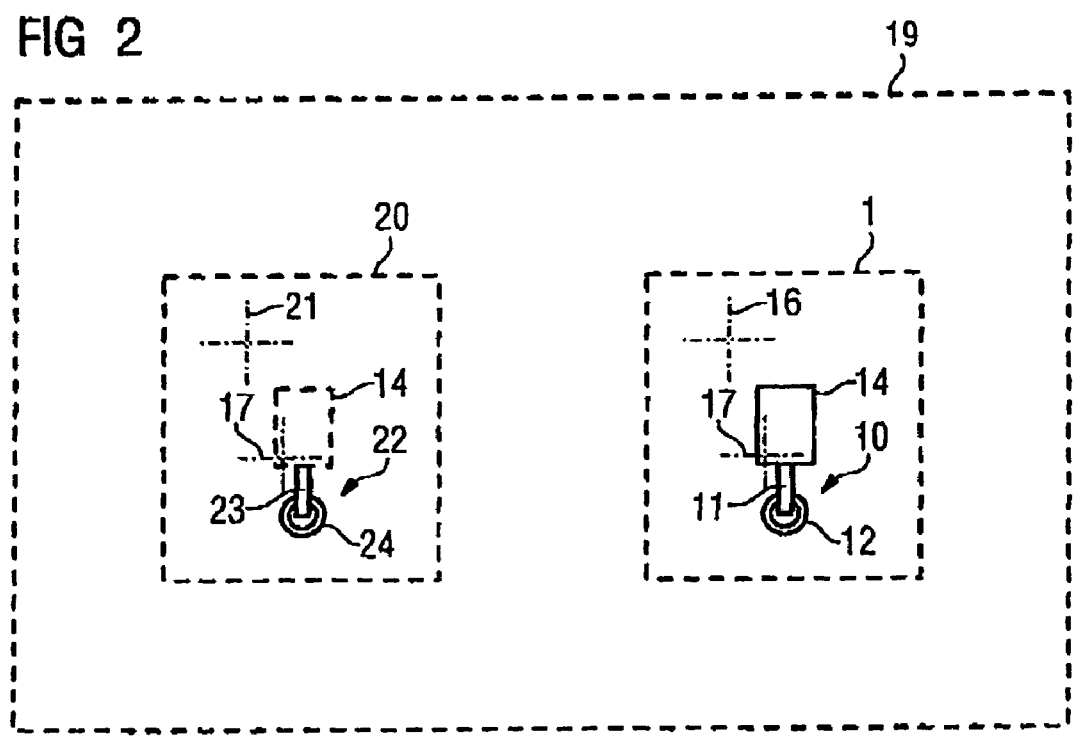

IMAGING DEVICE AND THERAPY FACILITY HAVING SUCH A DEVICE

The present patent document claims the benefit of the filing date of DE 10 2005 053 488.0, filed Nov. 9, 2005, which is hereby incorporated by reference.

BACKGROUND

1. Field

The present embodiments relate to an imaging device and a therapy facility having an imaging device.

2. Related Art

Three-dimensional picture data of the patient's body are typically used when planning for medical therapy, for example, in the field of radiation therapy. Before the actual therapy session, the body region to be treated, such as a tumor, is located as exactly as possible using the three-dimensional picture data. The picture data are typically recorded in an imaging step that precedes each treatment session so as to detect any spatial change in this body region compared to earlier treatments, for example, a change in size or shifting of a tumor in the body tissue.

Conventional medical imaging processes are used to generate the set of three-dimensional picture data. Examples of conventional medical imaging processes are, for example, computed tomography (CT), magnetic resonance tomography (MRI), positron emission tomography (PET), or single photon emission computed tomography (SPECT for short).

The term "radiation therapy", as described herein, includes both radiation therapy in the narrower sense, which applies high-energy electromagnetic radiation to tumor tissue, and particle therapy methods, which apply particle radiation (e.g. accelerated protons, carbon ions) to the tumor tissue.

The radiation therapy device has various machine settings, for example, the radiation direction. During radiation, for example, the position and the field size are typically defined relative to a predetermined patient isocenter, which is in the body of the patient and forms the origin of a patient coordinate system. The patient isocenter is placed, for example, in the center of the volume of a tumor that is visible in the three-dimensional picture data.

Generally, electronically controlled laser beams project lines onto the skin of the patient. The laser beam lines mark the location of the therapy point. The laser beam lines are drawn on the skin with ink markings and must remain visible until the next examination appointment or radiation appointment. If the ink markings fade or are erased, the lines must be redrawn.

SUMMARY

The present embodiments may obviate one or more of the limitations of the related art. For example, in one embodiment, an imaging device makes it simpler to plan and/or perform therapy, particularly radiation therapy.

In one embodiment, an imaging device includes a table that supports a patient and has an image-making unit that creates digital picture data of a body region of the patient. The image-making unit is embodied for three-dimensionally scaling the coordinates of the picture data recorded with respect to a space coordinate system that is stationary with the table and/or with respect to a table coordinate system that is stationary with a patient support of the table.

In one embodiment, the imaging device includes a table that supports a patient (hereinafter called an imaging table) and an image-making unit that creates digital picture data that represents a region in the interior of the patient's body. The image-making unit scales the coordinates of the picture data recorded not only with respect to a patient coordinate system but also with respect to a space coordinate system, relative to which the imaging table is mounted in stationary fashion. In another embodiment, the coordinates of the picture data are three-dimensionally scaled with respect to a table coordinate system which is defined in stationary fashion with regard to a patient support, for example, the "tabletop" of the imaging table.

As described herein, the term "scaling" is understood as "provide with a three-dimensional scale". In the course of the scaling, every pixel in the set of picture data is assigned a position or location information inside the space coordinate system and table coordinate system, which is, for example, a point in space. The scaling thus relates to the coordinates of the pixels within the picture data set. The scaling conversely does not contain any change in size, or the number of pixels in the picture data set.

As described herein, the term "space coordinate system" includes any coordinate system in which the imaging table is mounted in stationary fashion, or is in a constant spatial relationship with at least one fastening point of the imaging table. The space coordinate system can also be defined with regard to the surrounding imaging space. The imaging table is correspondingly mounted in stationary fashion relative to the surrounding imaging space. In one embodiment, movability of the imaging table relative to the surrounding imaging space may also be contemplated, for example, in the sense of a kinematic reversal. In this embodiment, the space coordinate system is moved jointly with the imaging table.

The space coordinate system and the table coordinate system essentially form equivalent or redundant reference systems that describe the location of a point in space in the imaging space. The present embodiments can utilize one or both of the systems. For example, in one embodiment, as long as the (optionally removable) patient support is connected to the imaging table, the table coordinate system and the space coordinate system are in a defined spatial relationship and can be converted between the two systems.

In one embodiment, the picture data created during a measurement have an absolute relationship with a region in space. The region in space is in a defined spatial relationship with the imaging device. The absolute relationship with a region in space is attained by scaling the coordinates of the picture data relative to the space coordinate system and the table coordinate system As a consequence of this defined spatial relationship, images can be reproduced that are identical or essentially identical in an especially simple and precise way. Accordingly, the location of a body region to be treated can be identified, for example, on or in the body of the patient, independent of ink markings. The invasive introduction of implanted markings (i.e. BBs) in the vicinity of the tumor can be avoided. Implanted markings may increase the attendant risks to the patient. In one embodiment, the imaging device comprises a computer tomography system (CT), magnetic resonance imaging system (MRI), positron emission tomography system (PET), or single photon emission computed tomography system (SPECT), and the digital picture data contains three-dimensional picture information.

For example, the imaging device is embodied as an X-ray system, such as a computed tomography system. Alternatively, the imaging device may also be embodied on the basis of some other imaging technique, for example, MRI, PET, or SPECT. The digital picture data include in particular three-dimensional picture information. The digital picture data form a 3D picture data set or volume data set. In an alternative embodiment, the digital picture data can include two-dimensional picture data as well.

The patient support of the imaging table is intended for immobilized and essentially replicable imaging of the patient. The patient support is embodied, for example, in the form of a stretcher. The patient support includes a foam plastic shell adapted individually to the patient to immobilize the patient, or other adjustable patient fixation devices. In an alternative embodiment, the patient support may be embodied as a chair, so that the patient is supported in a seated position.

In one embodiment, the patient support is reversibly removable from a fixedly mounted support arm of the imaging table. In this embodiment, the patient is subjected to further treatment steps while being immobilized and it is possible to save time during a treatment. In this embodiment, since the patient's body position no longer has to be changed once the patient isocenter has been located, the plan therapy can be precisely planned. An individually adapted patient support device can be coupled to the imaging device in a simple way.

To create replicable conditions with regard to placing the patient support on the support arm, the patient support can be secured to the support arm in only one defined position.

The support arm is adjustable, so that the patient support can be shifted relative to the space coordinate system in height and also horizontally (optional). The support arm is either manually adjustable or is embodied as a robot arm.

The image-making unit of the imaging device is movable relative to the imaging table. The image-making unit of the imaging device relative to the space coordinate system, for example, is displaceable on rails or the like in a defined direction of motion. The position of the image-making unit in the space coordinate system here is detected during the imaging operation by, for example, calibration of a motion controller of the image-making unit, by sensors, or in some other suitable way. The position of the image-making unit in the space coordinate system here is used as an input variable for scaling the coordinates of the picture data by using information stored in memory about the geometry of the image-making unit.

In one embodiment, a therapy facility, in addition to an imaging device, also includes a therapy device. The therapy device includes a radiation unit for radiation treatment of the patient using high-energy electromagnetic beams or accelerated particles. The therapy device is assigned a further space coordinate system, in which a table that supports the patient (hereinafter called a treatment table) is disposed in stationary fashion. In one embodiment, the therapy device is assigned an additional table coordinate system, which is disposed in stationary fashion with regard to a patient support of the treatment table.

In one embodiment, the imaging device and the therapy device are adapted to one another by suitable calibration or adjustment. The imaging device and the therapy device are adapted in such a way that a corresponding region in space in the space coordinate system or table coordinate system of the therapy device can be determined, for example, using the scaling and the position information of the coordinates of the picture data recorded by the imaging device and on the basis of a conversion code stored in memory. For example, the conversion code serves to convert the spatial volume of the imaging space. The volume is recorded in the picture data, into a corresponding spatial volume of the therapy space. In one embodiment using a conversion code, the point in space in the surroundings of the therapy device where a body region (i.e. tumor) of the patient that is reproduced in the picture data is located can be determined from the scaled picture data, for example, when the patient is supported on the treatment table. The scaled picture data can be used directly for planning therapy.

In one embodiment, the tables of the imaging device and of the therapy device are constructed and adjusted identically and are disposed identically with regard to the respective space coordinate system. In this embodiment, the conversion code is reduced to a factor of 1. For example, the position information of the picture data identically indicates the location of the reproduced body region of the patient supported in the therapy device in the associated space coordinate system or table coordinate system.

In one embodiment, the tables of the imaging device or therapy device are constructed or adjusted differently or are disposed differently with respect to the particular space coordinate system. In this embodiment, the conversion code that mediates between the two space coordinate systems is other than 1 and must be determined in an individual case from the specific local conditions. For instance, if the height of the treatment table is twice the height of the imaging table, then the scaling of the coordinates of the picture data is corrected by the conversion code with regard to the height by a factor of 2, and so forth.

In another embodiment, the treatment table has a removable patient support and a mechanical interface for coupling a patient support. The patient support and the interface are compatible with the corresponding parts of the imaging table. Embodying the two tables identically makes it possible to exchange the patient support between the imaging device and the therapy device, and, for example, transport the patient in the immobilized state.

BRIEF DESCRIPTION OF THE DRAWINGS

FIG. 1 is a schematic side view of one embodiment of an imaging device with an image-making unit and a table that supports and positions a patient; and FIG. 2 is a block diagram that illustrates one embodiment of a therapy facility having an imaging device and having a therapy device.

DETAILED DESCRIPTION

In one embodiment, as shown in FIG. 1, an imaging device 1 includes a computed tomography system 2 ("CT") as its image-making unit. The CT 2 includes a CT gantry 3 with a tunnel 4 into which a patient 5 is pushed during a CT examination. The CT gantry 2 is disposed and fixed displaceably on a rail system 6 in a displacement direction 7 on the floor 8 of an imaging space. The displacement direction 7 is oriented horizontally and is parallel to an isocentric axis 9 of the CT gantry 3. The patient's 5 body longitudinal axis is oriented along or parallel to the isocentric axis 9. Alternatively, the patient 5 is supported in inclined (i.e. perpendicular) fashion to the isocentric axis 9.

In another embodiment, the imaging device 1 includes a table 10 that supports and positions the patient 5 in the examination position. The table 10 includes a support arm 11, which is embodied as either a manually adjustable support arm or as a robot arm, and has one end fixed on the floor 8 in a stationary fashion with a support arm base 12. On one end of the support arm 11, spaced apart from the support arm base 12, a mechanical interface 13 is provided. A patient support 14 is mounted removably in a defined position on the support arm 11 using the mechanical interface 13, which supports the patient support 14. The patient support 14 is embodied as a stretcher (flat substrate). The patient support 14 also includes fixation devices 15, which keep the patient 5 immobilized in the intended examination position on the patient support 14. The fixation devices 15, for example, include a shell or hollow shape of foamed plastic. The fixation devices 15 are adapted individually to the patient 5, in which the patient's body or individual parts of his body are embedded for the examination.

In one embodiment, during a CT examination, the CT gantry 3 moves along the rail system 6 in the displacement direction 7, and the tunnel 4 is guided over the patient 5 located on the table 10, so that the patient 5 is moved through the tunnel 4 relative to the CT gantry 3.

In one embodiment, the imaging device 1 has a respective space coordinate system 16. The space coordinate system 16 is stationary in the imaging space. The table 10 is mounted in the space coordinate system 16 and is correspondingly in stationary fashion with its support arm base 12. In another embodiment, a table coordinate system 17 is defined with respect to the patient support 14. In one embodiment, as long as the patient support 14 is in turn coupled to the support arm 11 via the interface 13 between the space coordinate system 16 and the table coordinate system 17, a defined spatial relationship exists, which is dependent only on the support arm setting.

In one embodiment, a third coordinate system, hereinafter called the patient coordinate system 18, is conventionally defined relative to the patient's body. Alternatively, the patient coordinate system 18 represents purely an auxiliary variable, which is only optional and is defined concretely for the sake of illustration. The origin of the patient coordinate system 18 is typically placed at the center of a body region of the patient 5 that is to be treated and, for example, contains one or more tumors. The patient coordinate system 18 characterizes the position of the tumors within the patient's 5 body. In one exemplary embodiment, the patient coordinate system 18 and its origin (hereinafter called the patient isocenter) will be used to represent the body region to be treated.

In one embodiment, the coordinates of the picture data recorded by the imaging device 1 are not scaled (or at least not exclusively) with respect to the patient coordinate system 18 but instead with respect to the space coordinate system 16. For example, the absolute location of the patient isocenter in the space coordinates is ascertained and is converted into a therapy space.

In one embodiment utilizing CT 2 during the imaging, the travel position of the CT gantry 3 on the rail system 6 is detected. Using information stored in memory (not shown) about the orientation of the rail system 6 in the imaging space, the CT 2 is operative to calculate the position of the CT gantry 3 with respect to the space coordinate system 16. In another embodiment, additional information is stored in memory regarding the geometry of the CT gantry 3 (particularly about the height and location of the isocentric axis 9 in the imaging space), or the location of the recorded 3D picture data relative to the space coordinate system 16 that is determined from this information. Using the position information, the coordinates of the picture data are scaled. For example, the ascertained position information is stored in the memory together with the 3D picture data, so that an association can be made between the picture data and the imaged spatial volume, relative to the space coordinate system 16.

In one embodiment, the scaled picture data contains the information about the absolute position of the patient isocenter with regard to the space coordinate system 16, and with regard to the imaging space. If the support arm setting is changed, then the attendant shift in the patient isocenter in space is taken into account by a correction function, stored in memory, as a function of the support arm adjustment. For example, if the patient support 14 with the patient 5 immobilized on it is removed from the support arm 11 of the imaging device 1 and secured to the support arm of a different imaging or therapy space (not shown), the absolute location of the patient isocenter in the new imaging or therapy space is taken into account by a conversion code stored in memory (which for instance reflects a difference in size between the two support arms). In another embodiment, the position information of the 3D picture data may be identically transferred to the new imaging or therapy space. In another embodiment, if both support arms are identical to one another in their geometric construction, the support arm setting, and the position relative to a particular associated space coordinate system are also transferred.

In one embodiment, the coordinates of the 3D picture data are scaled with respect to the table coordinate system 17. The setting of the support arm 11 is also detected during the imaging. The setting of the support arm 11 and the information stored in memory about the position of the support arm base 12 in the imaging space and about the geometry of the support arm 11 can be used to determine the spatial relationship between the space coordinate system 16 and the table coordinate system 17. The position information of the 3D picture data recorded is mathematically converted from the space coordinate system 16 to the table coordinate system 17 using the spatial relationship.

Scaling the coordinates of the 3D picture data into units of the table coordinate system 17 defines the location of the patient isocenter solely with regard to the patient support 14. This has the advantage that this position information can still be used directly, even if the patient support 14 is removed from the support arm 11.

In one embodiment, as shown in FIG. 2, a therapy facility 19 includes (at least) one imaging space, in which an imaging device 1 is disposed, and (at least) one therapy space with a therapy device 20, which device includes a radiation unit (not further shown). The therapy facility 19 is used for radiation therapy. The above-described imaging device 1 can be used in the therapy facility 19. The therapy device 20 is assigned a space coordinate system 21, whose origin is placed in particular in the beam path of a therapy beam (not shown). In the case of a rotatable therapy beam (i.e. radiation gantry), the origin of the space coordinate system is placed in particular at the isocenter of the therapy beam.

In one embodiment, the therapy device 20 includes a table 22 with a support arm 23, which is constructed identically to the support arm 11 of the table 10 of the imaging device 1. The support arm 23 is mounted on a support arm base 24 in the same position relative to the space coordinate system 21 as the support arm 11 of the imaging device 1 is with regard to the space coordinate system 16. In an alternative embodiment, the support arms 11 and 23 may also be disposed differently with regard to the respective space coordinate system 16 and 21. In this embodiment, the different table arrangement is taken into account by an empirically ascertained correction code stored in memory.

In one embodiment, the tables 10 and 22 are mechanically identical. The tables 10 and 22 are equipped with identical patient supports 14, or can receive the same patient support 14 interchangeably.

In the course of a radiation therapy session, the patient 5 is first examined in the imaging device 1. For example, when planning the ensuing irradiation by recording the picture data, the location and extent of the tumors, or metastases that are to be treated are ascertained with respect to the space coordinate system 16 and/or the table coordinate system 17.

The patient support 14, with the patient 5 immobilized on it, is removed from the support arm 11 and taken to the therapy device 20, and there coupled to the support arm 23 of the table 22.

With the knowledge of the geometric construction of the tables 10 and 22, their disposition in the respective space coordinate systems 16 and 21, and the respective support arm position, the absolute position of the patient isocenter in the therapy space can be ascertained, with regard to the space coordinate system 21, by a conversion code stored in memory. If the tables 10 and 22 are identically constructed, disposed, and set, then the patient 5 is in the same position, for example, in the imaging device 1 and in the therapy device 20, relative to the space coordinate systems 16 and 21 of the respective imaging and therapy spaces.

In another embodiment, once the position of the patient isocenter in the space coordinate system 21 has been determined as described above, the patient 5 can be moved to the radiation position by adjusting the support arm 23. The shift in the patient isocenter in the space coordinate system 21 during the support arm adjustment is taken into account by a correction function stored in a memory. The radiation position is determined such that the patient isocenter is located at the origin of the space coordinate system 21, and in the beam path of the therapy beam, for example, in its isocenter.

In one embodiment, the 3D picture data recorded during the examination by the imaging device 1 and scaled to the space coordinate system 16 can consequently be used for planning therapy. Because of the absolute spatial relationship of the 3D picture data, it is unnecessary to create BB or ink markings in or on the patient 5.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. An imaging device comprising:
   a table that supports a patient; and
   an image-making unit operative to create digital picture data of a body region of the patient,
   wherein the image-making unit is operative to three-dimensionally scale the coordinates of the picture data recorded with respect to a space coordinate system that is stationary with the table, with respect to a table coordinate system that is stationary with a patient support of the table, or with respect to both the space coordinate system and the table coordinate system.

2. The imaging device as defined by claim 1,
   wherein the imaging device comprises a computer tomography system (CT), magnetic resonance imaging system (MRI), positron emission tomography system (PET), or single photon emission computed tomography system (SPECT), and wherein the digital picture data contain three-dimensional picture information.

3. The imaging device as defined by claim 1,
   wherein the table includes a patient support operative to support and position the patient and a support arm that supports the patient support, and wherein the support arm connects with a support arm base in stationary fashion with respect to the space coordinate system.

4. The imaging device as defined by claim 3, wherein the patient support is reversibly removable in a defined position on the support arm.

5. The imaging device as defined by claim 4,
   wherein the support arm is adjustable.

6. The imaging device as defined claim 5,
   wherein the image-making unit is movable relative to the space coordinate system, and the imaging device is operative to detect the position of the image-making unit relative to the space coordinate system, as an input variable for scaling the coordinates of the picture data.

7. A therapy facility comprising:
   an imaging device, and
   a therapy device that is operative to perform radiation therapy,
   wherein the therapy device includes a table that supports a patient, the table being disposed in stationary fashion with respect to a space coordinate system associated with the therapy device, a table coordinate system that is defined with regard to the patient support, or both the space coordinate system and table coordinate system, and
   wherein on the basis of a predetermined conversion code, a region in space corresponding to a picture data in the space coordinate system or table coordinate system of the therapy device is determined from a scaling of the coordinates of the picture data that is ascertained by the imaging device.

8. The therapy facility as defined by claim 7, wherein the table of the therapy device is identical to a table of the imaging device.

9. The therapy facility as defined by claim 8,
   wherein the table of the therapy device is disposed in stationary fashion relative to the space coordinate system associated with the therapy device in the same way as the table of the imaging device is disposed relative to the space coordinate system associated with it.

10. The imaging device as defined by claim 2,
    wherein the table includes a patient support that is operative to support and position the patient and a support arm that supports the patient support, and wherein the support arm is connected with a support arm base in stationary fashion with respect to the space coordinate system.

11. The imaging device as defined by claim 1, wherein the patient support is reversibly removable in a defined position on a support arm.

12. The imaging device as defined by claim 10, wherein the support arm is adjustable.

13. The imaging device as defined claim 10,
    wherein the image-making unit is movable relative to the space coordinate system, and the imaging device is operative to detect the position of the image-making unit relative to the space coordinate system, as an input variable that scales the coordinates of the picture data.

14. The therapy facility as defined by claim 7,
    wherein the table of the therapy device is disposed in stationary fashion relative to the space coordinate system associated with the therapy device in the same way as the table of the imaging device is disposed relative to the space coordinate system associated with it.

15. The therapy facility as defined by claim 7,
    wherein the imaging device comprises a table that supports a patient; and an image-making unit that is operative to create digital picture data of a body region of the patient, wherein the image-making unit is operative to three-dimensionally scale the coordinates of the picture data recorded with respect to a space coordinate system that is stationary with the table, with respect to a table coordinate system that is stationary with a patient support of the table, or with respect to both the space coordinate system and the table coordinate system.

16. The therapy facility as defined by claim 15,
wherein the table includes a patient support that is operative to support and position the patient and a support arm that supports the patient support, and wherein the support arm is connected with a support arm base in stationary fashion with respect to the space coordinate system.

17. The therapy facility as defined by claim 16, wherein the patient support is reversibly removable in a defined position on the support arm.

18. The therapy facility as defined by claim 17, wherein the support arm is adjustable.

19. The therapy facility as defined by claim 18,
wherein the image-making unit is movable relative to the space coordinate system, and the imaging device is operative to detect the position of the image-making unit relative to the space coordinate system, as an input variable that scales the coordinates of the picture data.

20. A method for providing medical therapy, the method comprising:
supporting a patient on a table;
recording and three-dimensionally scaling digital image data of a body region with respect to a space coordinate system that is stationary with the table, with respect to a table coordinate system that is stationary with a patient support of the table, or with respect to both the space coordinate system and the table coordinate system.

* * * * *